United States Patent [19]
Campbell

[11] Patent Number: 5,521,515
[45] Date of Patent: May 28, 1996

[54] FREQUENCY SCANNING CAPACIFLECTOR FOR CAPACITIVELY DETERMINING THE MATERIAL PROPERTIES

[75] Inventor: Charles E. Campbell, Laurel, Md.

[73] Assignee: The United States of America as represented by the Administrator of the National Aeronautics and Space Administration, Washington, D.C.

[21] Appl. No.: 394,108

[22] Filed: Feb. 17, 1995

[51] Int. Cl.⁶ .................................................. G01R 27/26
[52] U.S. Cl. ..................... 324/674; 324/662; 324/681; 324/686
[58] Field of Search .......................... 324/661, 662, 324/663, 671, 674, 681, 686, 690

[56] References Cited

U.S. PATENT DOCUMENTS

| | | | |
|---|---|---|---|
| 3,155,898 | 11/1964 | Chope | 324/674 X |
| 3,694,742 | 9/1972 | Bergmanis et al. | 324/674 X |
| 4,322,678 | 3/1982 | Capots et al. | 324/674 X |
| 4,336,493 | 6/1982 | Gregory et al. | 324/674 X |
| 4,370,611 | 1/1983 | Gregory et al. | 324/674 X |
| 4,433,286 | 2/1984 | Cabots et al. | 324/674 X |
| 4,881,025 | 11/1989 | Gregory | 324/671 X |
| 5,214,388 | 5/1993 | Vranish et al. | 324/681 X |
| 5,363,051 | 11/1994 | Jenstrom et al. | 324/661 |
| 5,373,245 | 12/1994 | Vranish | 324/662 |
| 5,442,347 | 8/1995 | Vranish | 324/686 X |

Primary Examiner—Kenneth A. Wieder
Assistant Examiner—Diep Do
Attorney, Agent, or Firm—Robert D. Marchant

[57] ABSTRACT

A capaciflector sensor system scanned in frequency is used to detect the permittivity of the material of an object being sensed. A capaciflector sensor element, coupled to current-measuring voltage follower circuitry, is driven by a frequency swept oscillator and generates an output which corresponds to capacity as a function of the input frequency. This swept frequency information is fed into apparatus e.g. a digital computer for comparing the shape of the capacitance vs. frequency curve against characteristic capacitor vs. frequency curves for a variety of different materials which are stored, for example, in a digital memory of the computer or a database. Using a technique of pattern matching, a determination is made as to the identification of the material. Also, when desirable, the distance between the sensor and the object can be determined.

20 Claims, 2 Drawing Sheets

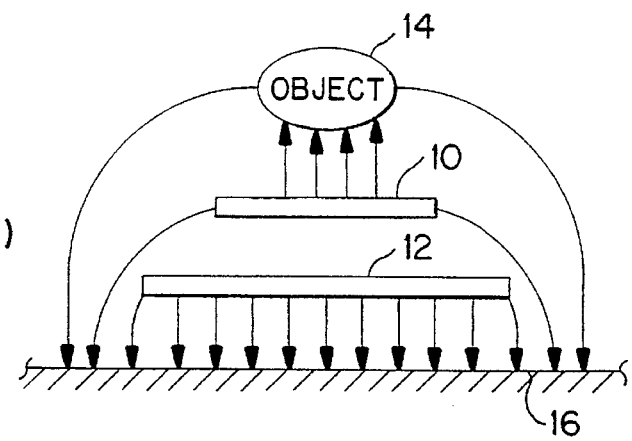
FIG. 1
(PRIOR ART)
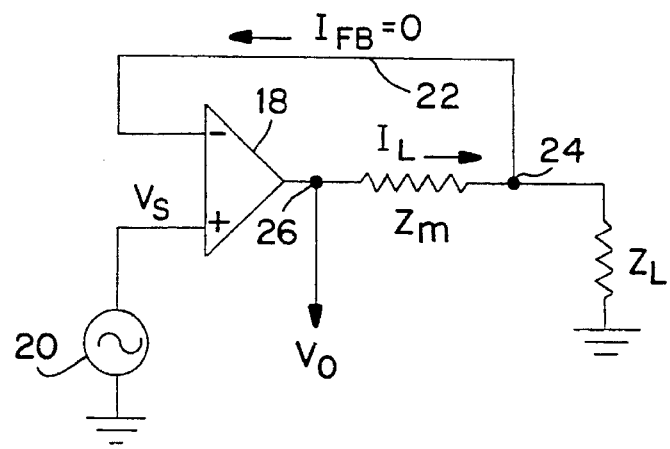
FIG. 2
(PRIOR ART)
FIG. 3
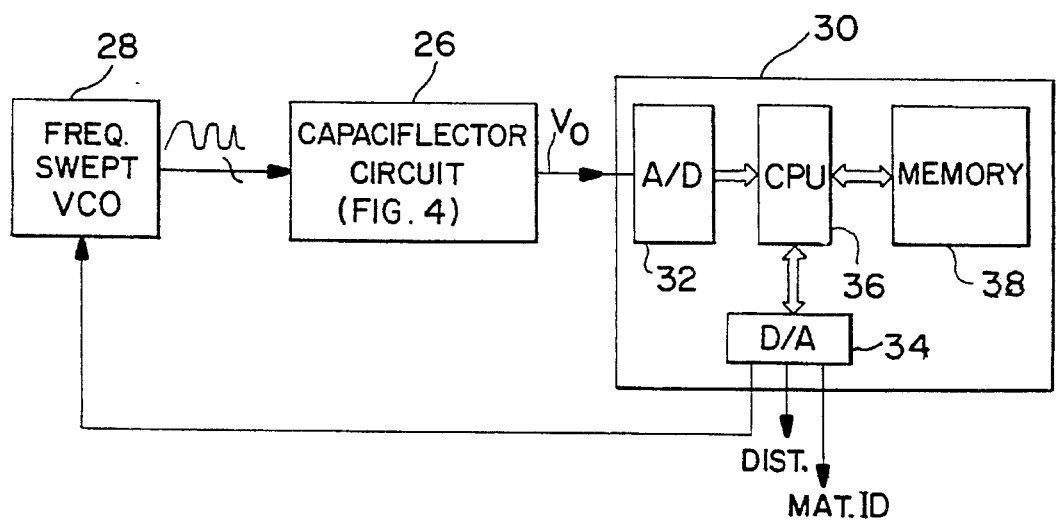

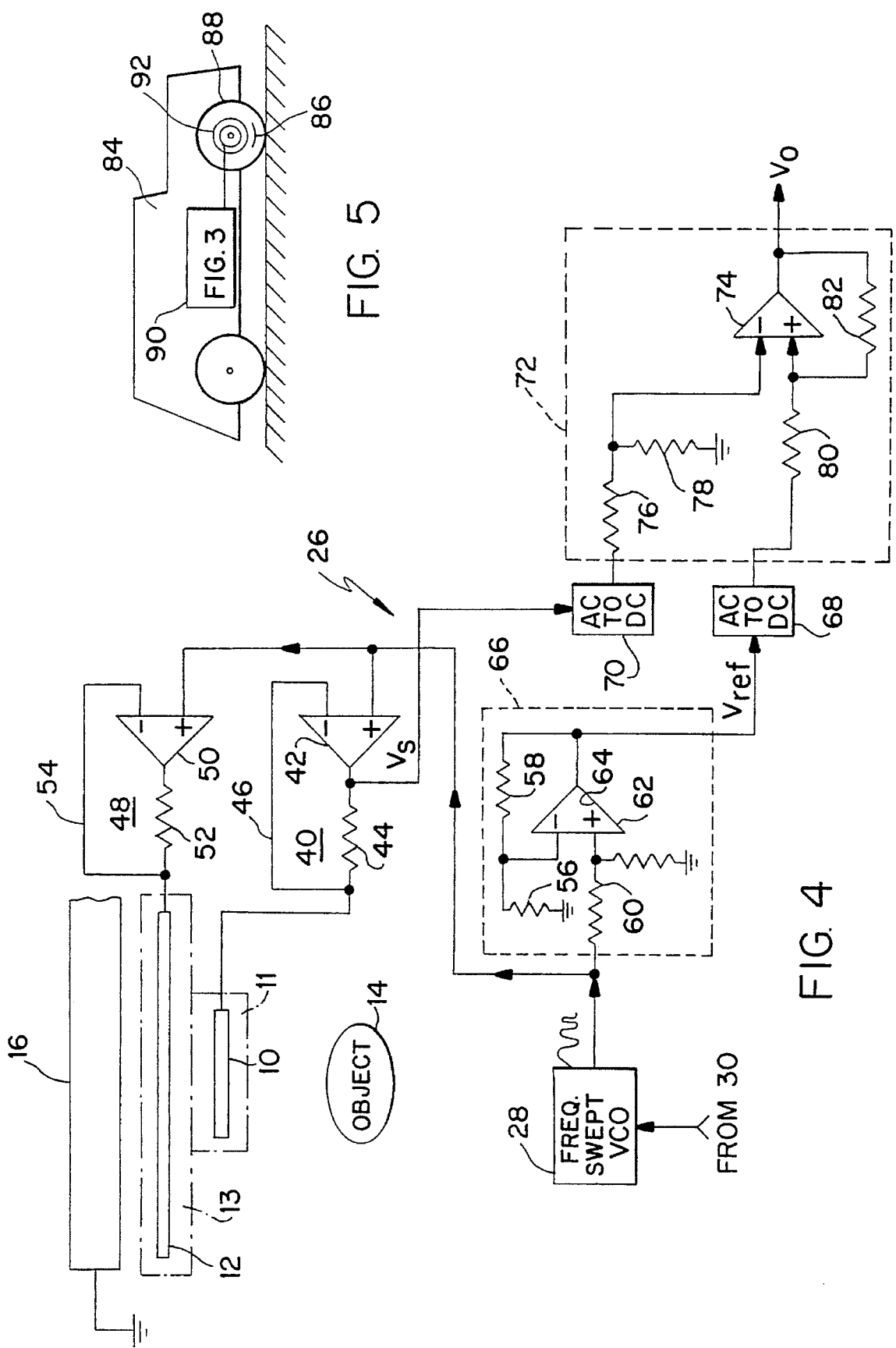

FREQUENCY SCANNING CAPACIFLECTOR FOR CAPACITIVELY DETERMINING THE MATERIAL PROPERTIES

ORIGIN OF THE INVENTION

The invention described herein was made by an employee of the United States Government, and may be manufactured and used by and for the Government for Governmental purposes without the payment of any royalties thereon or therefore.

CROSS-REFERENCE TO RELATED APPLICATIONS

This invention is related to an invention shown and described in:

(1) U.S. Ser. No. 08/189,344 (Attorney Docket No. GSC 13563-1), entitled "Current Measuring OP-AMP Devices", filed in the name of John M. Vranish on Jan. 31, 1994, pending;

(2) U.S. Ser. No. 08/008,426 (Attorney Docket No. GSC 13541-1) entitled "Double Driven Shield Capacitive Type Proximity Sensor", filed in the name of John M. Vranish on Jan. 25, 1993, now U.S. Pat. No. 5,442,347; and (3) U.S. Ser. No. 08/090,230 (Attorney Docket No. GSC 13564-1) entitled "Capaciflector Camera", filed in the name of John M. Vranish on Jul. 12, 1993, now U.S. Pat. No. 5,373,245.

The above related applications are assigned to the assignee of the present invention. Moreover, the teachings of these related applications are meant to be incorporated herein by reference.

BACKGROUND OF THE INVENTION

1. Field of the Invention

The Present Invention relates generally to capacitive type sensor apparatus, and more particularly to a method and a capacitive type "Capaciflector" proximity sensor for sensing the type of material in the object being approached by the sensor.

2. Description of the Prior Art

Capaciflector type proximity sensors are well known having been first disclosed in U.S. Pat. No. 5,166,679, entitled "Driven Shielding Capacitive Proximity Sensor", issued to John M. Vranish on Nov. 24, 1992. There, a capacitive type proximity sensing element is backed by a reflective shield, with the shield being driven by an operational amplifier (op-amp) at the same voltage as and in phase with the sensing element. The shield is used to reflect the sensing element's electric field lines away from a grounded surface towards an intruding object and thus substantially increasing the sensor's range and sensitivity. The output signal from the sensing element is coupled to an oscillator circuit whose output is inversely proportional to the capacitance between the sensor and ground. Such a sensor system is relatively simple and yet has the ability to sense virtually any object it encounters.

In the related U.S. patent application U.S. Ser. No. 08/189,344 entitled "Current-Measuring OP-AMP Devices," referenced above, there is disclosed an electrical circuit called a current-measuring voltage follower which is in effect a micro miniature precision high-gain servo system in which voltage applied to one terminal of an operational amplifier (op-amp) is servoed through the op-amp to its other input terminal. The op-amp acts as a current source having a low impedance output. Therefore when such a current-measuring voltage follower circuit is inserted between a voltage source and the sensor element and the shield of a capaciflector proximity sensor, the current through the sensor will vary according to what it senses and is measured thereby.

Prior art capaciflector circuits also operate at single frequencies, i.e. the capaciflector operates at a set frequency, although the selected frequency can differ between different capaciflectors. Thus it provides capacitance measurements at a single frequency and although it is affected by the permittivity of nearby objects it does not provide sufficient information to identify the target object's material composition. Thus know prior art capaciflector systems cannot identify materials by their composition.

Known prior art apparatus for detecting the composition of material typically includes such apparatus as a gamma ray spectrometer. This type of device utilizes radiation to obtain a characteristic excitation curve which is used to identify materials by their elemental composition. A gamma ray spectrometer, however, takes a relatively long period of time, e.g. 10 minutes, of "staring" at a target to acquire its data. Furthermore, different materials may have the same elemental composition such as sand and quartz and thus appears to a gamma ray spectrometer as the same thing. Another problem with a gamma ray spectrometer is its radioactive nature.

Also, the concept of frequency scanning is generally well known and is utilized in such apparatus as radar where it is referred to as "chirping". Radar, however, is used for distance detection using far field techniques and does not operate in the near field.

SUMMARY

It is therefore an object of the present invention to provide a sensor capable of providing information on both distance to and composition of materials being sensed.

Another object of the present invention is to provide a capaciflector type sensor system which can detect the permittivity vs. frequency signature of different types of materials.

It is a further object of the present invention to provide a capaciflector system which can identify various types of material in relatively harsh environments while not being affected thereby.

The foregoing and other objects of this invention are achieved by a frequency scanning capaciflector system which is capable of detecting both the permittivity of the material of an object being sensed as well as its distance from a capaciflector sensor. A capaciflector sensor, coupled to current-measuring voltage follower circuitry, is driven by an oscillator which is swept in frequency and generates an output which corresponds to capacity as a function of the input frequency. This swept frequency information is fed into apparatus for comparing the shape of the capacitance vs. frequency curve against characteristic capacitor vs. frequency curves for a variety of different materials which are stored, for example, in a digital memory or a database. Using a technique of pattern matching in apparatus such as a digital computer, a determination is made as to the identification of the material and the distance away from an object being sensed.

A BRIEF DESCRIPTION OF THE DRAWINGS

The following detailed description of the invention will be more readily understood when considered together with the accompanying drawings in which:

FIG. 1 is a diagram generally illustrative of a conventional capaciflector type proximity sensor;

FIG. 2 is an electrical schematic diagram illustrative of a simplified known prior art current-measuring voltage follower circuit;

FIG. 3 is a simplified electrical block diagram broadly illustrative of the subject invention;

FIG. 4 is an electrical schematic diagram illustrative of an embodiment for implementing the capaciflector circuit shown in FIG. 3; and FIG. 5 is a diagram illustrative of one application for the subject invention.

DETAILED DESCRIPTION OF THE INVENTION

This invention utilizes a capacitive sensing element termed a "capaciflector". Such a device is shown in FIG. 1 and includes a sensing element 10 which is backed by a reflector element or shield 12 and which is located between an object 14 and a reference device and/or ground plane 16. The shield member 12 and the capacitive sensor 18 are driven at the same instantaneous voltage and generates an electric field distribution as shown. It can be seen that the shield member 12 substantially prevents the electric field of the sensing element 10 from returning directly to the ground plane 16, but centers the field concentration between the sensor 10 and the object 14. In U.S. Pat. No. 5,166,679, the output signal from the sensor 10 is coupled to an oscillator circuit, not shown, whose output is inversely proportional to the capacitance between the object 14 and the ground plane, thus providing a capacitive type distance measuring device.

In the above cross-referenced U.S. patent application Ser. No. 08/189,344, entitled "Current-Measuring Op-Amp Devices", there is disclosed electronic circuit architecture, as shown in FIG. 2, which is particularly useful in connection with the capaciflector arrangement shown in FIG. 1 and is referred to as a "current-measuring voltage follower". The current-measuring voltage follower as shown in FIG. 2 is comprised of an operational amplifier (op-amp) 18 which has an AC voltage input from a source 20 coupled to the (+) input terminal and whose output terminal is coupled to a load impedance $Z_L$ through a current-measuring impedance $Z_m$. A direct connection 22 is made back to the (−) input terminal from a circuit node 24 between the load impedance $Z_L$ and the current measuring impedance $Z_m$. The op-amp 18 acts as a high gain servosystem such that the source voltage $V_s$ is servoed through the op-amp 18 to its (−) terminal. Such a configuration comprises a current source with a low impedance output. If the feedback loop 22 is such that the magnitude of the feedback current $I_{fb} = 0$, then the current out of the operational amplifier 18 is equal to the load current $I_L$ being coupled to ground through the impedances $Z_m$ and $Z_L$. Also there is an output voltage $V_0$ generated which appears at circuit node 26 and which is also proportional to $I_L$.

The present invention utilizes current-measuring voltage follower circuitry as shown in FIG. 2, where $Z_L$ comprises the sensor element 12 or the shield 10 (FIG. 1) and is a modification both of the capaciflector concept and current-measuring voltage follower technology in that it now includes a frequency scanning technique for comparing sensed capacitance data over a predetermined swept frequency range with the capacitance/permittivity signatures of known materials to provide not only distance approximations, but also enables the system to respond to the type of material being sensed. This is accomplished while retaining the robust feature of the capaciflector, i.e. being able to operate in harsh environments such as vacuum, poisonous gas, dirt and dust, etc.

Since a capaciflector sensor measures capacitance, the capacitance measured is not only a function of geometry, including the distance between the sensor 10 and nearby objects, such as the object 14 shown in FIG. 1, but also the permittivity of the object 10 itself.

The effect of the object's permittivity can be demonstrated using a parallel plate capacitor model where the capacitance C is expressed by:

$$C = \epsilon A/d \tag{1}$$

where $\epsilon$ is the permittivity of the material between the plates of the capacitor, A is the area of the plates, and d is the distance between the plates. The capaciflector as shown in FIG. 1 can be thought of as two capacitors in series, not shown, where one capacitor is that existing between the sensor 10 and the face of the object 14 and the other from the object 14 to ground 16. The latter capacitor, which may be better modelled as a capacitor and a resistor in parallel, also not shown, has a capacitance controlled by the geometry and permittivity of the object 14.

The present invention is therefore based upon the concept that given a pair of parallel plate capacitors in series, and making a plurality of measurements at different frequencies, one can solve for both permittivity and distance independently of one another. Accordingly, a capaciflector such as shown in FIG. 1, is used in order to differentiate the effect of permittivity from the geometry of the object by generating and using the shape of the capacitance curve as a function of frequency. Since materials have characteristic permittivity vs. frequency curves independent of the shape of the object or its distance from the sensor, the shape of the capacitance vs. frequency curve will be a function of the constituency of the material in nearby objects if one ignores an unknown amplitude factor which is due to geometry.

Since a database or a digital computer including a memory can store a large number of capaciflector response vs. frequency curves for a large variety of materials, the present invention comprises a system, as shown in FIG. 3, where a capaciflector circuit 26, the details of which are shown in FIG. 4, is driven by a voltage controlled oscillator 28 which is swept in frequency under the control of a digital computer 30 including analog to digital (A/D) and digital to analog (D/A) boards 32 and 34, a central processing unit (CPU) 36 and a memory 38 for storing capaciflector response vs. frequency curves. The computer 30 controls the frequency of the VCO 28 so that it typically operates at low frequencies, in the range between 100 Hz–3 MHz and at low voltages, typically 10 volts or less. Thus it is not intended to radiate energy and is not harmful to operating personnel.

The CPU 36 operate to compare the signal $V_0$ corresponding to the measured capacitive response curve of the frequencies swept capaciflector circuit 26 with stored response curves in the memory 38 using a mean-squared estimator with amplitude as a free variable which can be expressed as:

$$\min_{a,m} \Sigma_f \{ ar_{f,m} - c_f \}^2$$

where a is the amplitude of the unknown, $r_{f,m}$ is the stored response of material m at frequency f, and c is the current capaciflector response as frequency f. This corresponds to a one "fits a line" to the triplet $\{f, r_{f,m}, c_f\}$ which comprises a three dimensional line fitting operation and where a material m is chosen which produces a minimum mean-squared area.

It should be noted that when desirable other pattern matching and classification techniques can be utilized such as neural nets, etc.

Referring now to FIG. 4, shown thereat are the details of the capaciflector circuitry 26 shown in FIG. 3. In FIG. 4 the sensor element 10 and the shield 12 which are mutually separated from each other as well as the ground plane 16 which may be, for example, the platform upon which the components 10 and 12 are mounted are separated by electrical insulation material shown by reference numerals 11 and 13. The frequency swept VCO 28 is coupled to the sensor element 10 by means of a first current-measuring voltage follower circuit comprised of op-amp 42, resistor 44, and a direct feedback connection 46 to the (−) input terminal. The output of the swept VCO 28 is connected to the (+) input. A second current-measuring voltage follower circuit 48 couples the output of the VCO 28 to the shield 12. The voltage follower 48 is comprised of an op-amp 50, a resistor 52, and a direct feedback circuit connection 54 to the (−) input of the op-amp 50. As in the first voltage follower circuit 40, the output of the VCO 28 is coupled to the (+) input of op-amp 50.

Such an arrangement effectively locks both sensor 10 and shield 12 to the voltage source 28, and to each other, and therefore the electrical fields of the shield 12 serve to block the path of the electrical fields of the sensor 10 to ground 16, resulting in a "capaciflector action" and with it increased range and sensitivity.

The remaining components of FIG. 4 represent standard electronic circuits. Resistors 56, 58, 60, 62 and op-amp 64 comprise a reference circuit 66 which extracts a reference voltage $V_{ref}$ from the VCO source 28. This reference voltage is converted to a DC voltage by means of an AC to DC converter 68. A current-measurement output signal $V_s$ of the sensor 10 and generated by the current-measuring voltage follower circuit 40 is converted to DC by a second AC to DC converter 70. The outputs of the AC to DC converters 68 and 70 are fed to a differential amplifier circuit 72 comprised of an op-amp 74 and resistors 76, 78, 80 and 82, with an amplified difference signal $V_0$ between $V_s$ and $V_{ref}$ being outputted therefrom and which is then fed to the A/D board of the computer 30 shown in FIG. 3.

The frequency scanning capaciflector of FIG. 3 provides material composition information for objects in the sensor's field of view (1–2 feet) depending upon the sensor's geometry. The geometry of the sensor element 10, however, is highly flexible. The sensor 10 and shield 12 must be good conductors, and therefore can, when desirable, be solid bars of steel or thin strips of copper. The insulator materials 11 and 13 can be tape, plastic, kevlar, etc. The outer insulator is not strictly required, as the electronics can be made to permit short circuits. The sensor 10 can also be a tool as well as a separate sensor strip (such as a wrench or probe).

Frequency scanning capaciflectors according to this invention can be placed close to one another in a "camera" configuration such as taught in the above referenced application Ser. No. 08/090,230, entitled "Capaciflector Camera" and can include, for example, sensor dots, interwoven mesh, etc., sharing a single shield. The frequency scanner's output could also be converted to audio, allowing a person to position the sensor to optimize some perceived signal to move a rover towards some material, for example.

The frequency scanning capaciflector of this invention can also be used in any number of applications. For example, as shown in FIG. 5, if a vehicle 84 includes a capaciflector sensor element 86 in one of its tires 88 and is coupled to apparatus 90 included in the embodiment of FIG. 3, being coupled thereto by slip rings 92 or other type of coupling device, one could determine the composition of the material under the tire 88 of the vehicle 84. This would be of particular utility as a soil information detector which would allow vehicles to drive over sites and thereby make maps of soil types, water contents, etc. of the terrain over which the vehicle 84 passes. It would also have use in extra planetary rovers and thus could be used for exploration purposes. It could also be used as a dirt/dust sensor since a frequency scanning capaciflector could pick up the permittivity vs. frequency signature of dust and identify its bulk composition. Also, this invention could detect humans in a variety of settings. Since humans are mostly water, they would have radically different permittivity vs. frequency responses as compared to surrounding environment. This includes heavy equipment which may operate near people, such as bulldozers, various agricultural machinery, forklifts and the like.

Thus what has been shown and described is a capaciflector configuration and method utilizing same which permits one to extract information on both distance to and composition of nearby materials while being able to operate in practically in any environment which would not physically harm the apparatus.

Having thus shown and described what is at present considered to be the preferred method and embodiment for practicing the subject invention, it should be noted that the same has been made by way of illustration and not limitation. Accordingly, all modifications, alterations and changes coming within the spirit and scope of the invention as set forth in the appended claims are herein meant to be included.

I claim:

1. Apparatus for capacitively determining the material composition of an object being approached, comprising:

a capacitive type sensor including a sensor element and at least one shield member located between said object and a reference potential surface, said shield member being of a size substantially larger than said sensor element for reducing the parasitic capacitance between said sensor element and said reference potential surface;

signal generating means for generating a signal varied in frequency over a predetermined frequency range;

circuit means for commonly coupling said signal generator means to said sensor element and said shield member;

means coupled at least to said sensor element for detecting a capacitance vs. frequency characteristic of the capacitance between said sensor element and said object over said frequency range;

means for storing a plurality of capacitance vs. frequency characteristics, each of said characteristics being a respective characteristic of a plurality of different constituent materials; and means for comparing the detected capacitance vs. frequency characteristic of the capacitance between said sensor element and said object against said plurality of capacitance vs. frequency characteristics for matching and thereby identifying the constituent material of said object.

2. The apparatus as defined by claim 1 wherein said capacitive type sensor comprises a capaciflector sensor.

3. The apparatus as defined by claim 2 wherein said signal generator means comprises a frequency swept signal generator.

4. The apparatus as defined by claim 3 wherein said means for commonly coupling said frequency swept signal generator to said sensor element and said shield member comprises voltage follower circuit means.

5. The apparatus as defined by claim 4 wherein said voltage follower circuit means comprises first and second current-measuring voltage follower circuits respectively coupled to said sensor element and said shield member.

6. The apparatus as defined by claim 5 wherein said first and second current-measuring voltage follower circuits each comprises an operational amplifier having first and second input terminals and an output terminal, a current-measuring impedance coupled between said output terminal and a load impedance comprised of one element or member of said sensor element and said shield member, and feedback circuit means coupled between a first circuit node intermediate said load impedance and one input of said first and second input terminals and wherein said frequency swept signal generator is coupled to the other of said first and second input terminals.

7. The apparatus as defined by claim 6 wherein said feedback circuit means comprises a direct connection between said first circuit node and said one input of said operational amplifier.

8. The apparatus as defined by claim 7 wherein said current-measuring impedance comprises a current-measuring resistor and wherein said means for detecting said capacitance vs. frequency characteristic comprises means for detecting a voltage across said current-measuring resistor corresponding to a capacitance measurement of the capacitance between said sensor element and said object.

9. The apparatus as defined by claim 8 wherein said means for detecting said capacitance vs. frequency characteristic includes a second circuit node intermediate said output terminal and said current-measuring resistor.

10. The apparatus as defined by claim 9 wherein said means for comparing includes computer circuit means.

11. The apparatus as defined by claim 10 wherein said computer circuit means comprises digital computer means and wherein said means for storing comprises a digital memory.

12. The apparatus as defined by claim 11 and additionally including means for converting said voltage corresponding to a capacitance measurement to a digital voltage signal.

13. The apparatus as defined by claim 12 wherein said digital computer means performs a capacitance vs. frequency characteristic comparison using a mean-square estimator with amplitude as a free variable and which is expressed as:

$$\min_{a,m} \Sigma_f \{ ar_{f,m} - C_f \}^2$$

where a is an unknown amplitude, $r_{f,m}$ is a stored capacitance vs. frequency characteristic of the material composition of said object at a frequency f, and C is the measured capacitance vs. frequency characteristic of the material composition of said object at the frequency f, and wherein said digital computer means generates an output signal of material composition m of a minimum mean-squared error, thereby identifying the material composition of said object sensed by said sensor element.

14. The apparatus as defined by claim 12 and additionally including reference circuit means coupled to said frequency swept signal generator for generating a reference signal, and differencing circuit means coupled to said second circuit node of said means for detecting and said reference circuit means for generating a differential output signal of said reference signal and said capacitance measurement voltage, said differential output signal being coupled as an input to said digital computer means.

15. The apparatus as defined by claim 14 and additionally including first and second AC to DC converter means respectively coupling between said second circuit node and said reference circuit means to said differencing circuit.

16. A method for capacitively determining the material composition of an object, comprising the steps of:

generating a signal swept in frequency over a predetermined frequency range;

coupling said signal swept in frequency to a sensor element and to a shield member of a capaciflector type sensor located between said object and a reference potential surface;

detecting a capacitance vs. frequency characteristic of the capacitance between said sensor element and said object over said frequency range;

storing a plurality of capacitance vs. frequency characteristics of a plurality of different object materials; and comparing and matching the capacitance vs. frequency characteristic of the capacitance between said sensor element and said object against said plurality of stored capacitance vs. frequency characteristics for identifying the constituent material of said object.

17. The method of claim 16 wherein said step of detecting includes sensing the output of a current-measuring voltage follower circuit coupled between a swept frequency signal generator generating said signal swept in frequency and said sensor element.

18. The method of claim 17 wherein said step of storing comprises digitally storing said plurality of capacitance vs. frequency characteristics and wherein said step of comparing comprises digitally comparing a capacitance vs. frequency characteristic between said sensor element and said object with said digitally stored plurality of capacitance vs. frequency characteristics.

19. The method of claim 18 wherein said step of digitally comparing includes a comparing step using a mean-square estimator with amplitude as a free variable.

20. The method of claim 19 wherein said comparing step operates according to the expression:

$$\min_{a,m} \Sigma_f \{ ar_{f,m} - C_f \}^2$$

where a is an unknown amplitude, $r_{f,m}$ is a stored capacitance vs. frequency characteristic of the material composition of said object at a frequency f, and C is the measured capacitance vs. frequency characteristic of the material composition of said object at the frequency f.

* * * * *